US00PP08115P

United States Patent [19]

Kanato et al.

[11] Patent Number: Plant 8,115

[45] Date of Patent: Jan. 26, 1993

[54] JAPANESE PEAR TREE "YASATO"

[75] Inventors: Kitsuo Kanato, Nagoya; Yutaka Machida; Akio Kurihara, both of Tsuchiura; Yoshihiko Sato; Kazuyuki Abe, both of Tsukuba; Ichiro Kajiura, Fujisawa; Kanetsugu Seike, Tokyo; Kazuo Kotobuki, Nakagun; Isao Shimura, Machida; Teruo Kozono, Tsukuba; Tatsushi Ogata, Minamitakaki; Mitsuo Omura, Shizuoka, all of Japan

[73] Assignee: Fruit Tree Research Station, Ministry of Agriculture, Forestry and Fisheries, Tsukuba, Japan

[21] Appl. No.: 667,930

[22] Filed: Mar. 12, 1991

[51] Int. Cl.[5] ..... A01H 5/00

[52] U.S. Cl. ..... Plt./36

[58] Field of Search ..... Plt./36

*Primary Examiner*—James R. Feyrer

*Attorney, Agent, or Firm*—Armstrong & Kubovcik

[57] ABSTRACT

Disclosed is a Japanese pear tree bearing fruit with light green yellow skin, having a strong vigor, a stout shoot and a long internode, a high resistance to scab, and a high productivity. This tree produces a circular-ellipse-shaped fruit which matures early in the season, i.e., from the middle to the end of August, in the central part of the Kantō district, Japan. The fruit has a medium size and the same weight as "Chikusui", i.e., 250 to 300 g, and a yellowish white flesh which is soft, crisp and very juicy with a high Brix, the pH of the juicy being about 4.7–4.8, and little aromatic flavor, thus having an excellent dessert quality.

5 Drawing Sheets

BACKGROUND OF THE VARIETY

The present invention relates to a new and distinct variety of Japanese pear tree (*Pyrus pyrifiolia* Nakai) bearing fruit with a yellowish-green skin, having a stout shoot and a long internode, strongly resistant to black spot disease, and having a high productivity.

In Japan, excellent cultivars, including 'Kōsui', 'Shinsui' and Hōsui known as "Sansui", have been bred for a Japanese pear tree bearing a fruit with a yellowish-brown skin, and thus producers of pears were able to cultivate both early and mid-season varieties of the pear tree bearing a fruit with a yellowish-brown skin. Regarding a Japanese pear tree bearing a fruit with a yellowish-green skin, 'Nijisseiki' is the best known cultivated species; others, for example, 'Yakumo' and 'Shinseiki', are little-cultivated species. Thus, desirably the term of distribution of the pear fruit is extended, particularly using an early cultivar, and thus a useful early cultivar having a fruit that is soft, crisp and very juicy, with a high Brix, is required.

One purpose of our breeding program is to provide improved varieties of the pear fruit tree which can be picked earlier in the season than 'Nijisseiki'.

ORIGIN AND ASEXUAL REPRODUCTION OF THE VARIETY

The new variety of Japanese pear tree is a cross-seedling which originated from a crossing between 'Hakko' (♀), which is an early cultivar bearing a fruit with a yellowish-green skin and having a weak sweetness of the flesh, and '75-23' (♂), which was derived from crossing 'Nijisseiki' and "RI-14" and is a mid-season variety bearing a fruit with a yellowish-green skin, in 1972 at the Horticultural Research Station of the Ministry of Agriculture, Forestry and Fisheries, at Hiratsuka-shi, Kanagawa-ken, Japan. The tree was kept in a nursery for a long time, and then was planted, in 1976, at the Research Station at Tsukuba-shi, Ibaraki-ken, Japan. The tree bore fruit for the first time in 1978, and both the maturation period and the quality of the fruit corresponded to the above-mentioned purpose. Accordingly, the tree was selected as the first selection in 1982, and subjected to local adaptability tests, from 1983, at 34 of the experimental stations in the main pear growing regions, such as Saitama-ken, Japan, under strain number 'Tsukuba No. 38'. As a result, this new variety of Japanese pear tree according to this invention was judged to be an excellent new cultivar, and was denominated 'Yasato' in 1989.

We asexually reproduced this new and distinct variety of Japanese pear tree 'Yasato', by grafting, at the Fruit Tree Research Station, Ministry of Agriculture, Forestry and Fisheries, at 2-1, Fujimoto, Tsukuba-shi, Ibaraki-ken, Japan, and confirmed the homogeneity and stability of 'Yasato' according to this invention.

An application for this new variety of Japanese pear tree 'Yasato' under the Seeds and Seedling Law of Japan was filed on Mar. 31, 1989, under application number 3331, and is now pending.

SUMMARY OF THE VARIETY

This new variety of Japanese pear tree has a strong vigor, a strong trunk and a long internode, compared with 'Chikusui' and 'Shuugyoku', and almost the same flowering time as 'Chikusui', a high productivity and a high quality fruit, compared with both 'Yakumo' and 'Shinesiki', an affinity to 'Nijisseiki' in connection with pollination, and is highly resistant to black spot disease. The tree has a width of about 8 meters and a height of about 2.5 meters when the tree is treated with trellis training to a height of about 1.8 meters. The tree has a medium branching habit and branch density in an unpruned or a slightly pruned state. When the tree is conventionally treated with trellis training and pruned, vegetative shoots and succulent spouts grow well, and further, the tree canopy is quickly extended. When the tree is about ten years old, it has three primary scaffold branches, the branch being about 4 to 5 meters long. When a ten year old tree was cultivated in the central part of the Kantō district, e.g., Kanagawa prefecture, Japan, a vegetative shoot of same was extended by 70–80 cm per year, on average. The crotch angles formed by branches are about 47 degrees. The tree produces a circular-ellipse-shaped fruit which matures early in the season, i.e., from the middle to the end of August, in the central part of Kantō district, Japan. The fruit has a medium size and the same weight as 'Chikusui', i.e., 250 to 300 g, a yellowish-green skin, and a white flesh which is soft and crisp. The fruit juice has a high Brix, and a low acidity at a pH of about 4.79.

DESCRIPTION OF THE VARIETY

Figure 1:
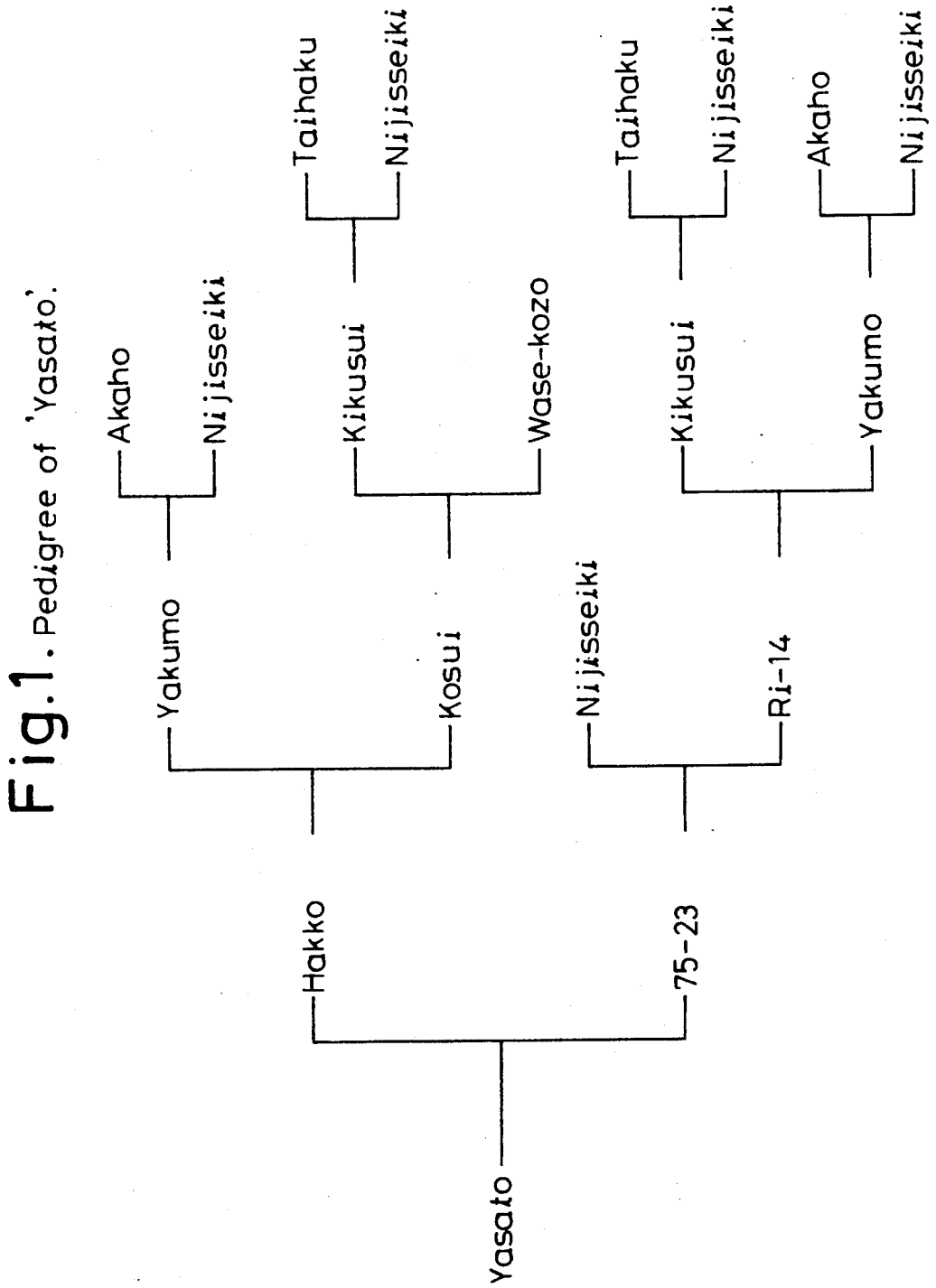
FIG. 1 gives the pedigree of the new and distinct variety of Japanese pear tree 'Yasato'.
Figure 2:
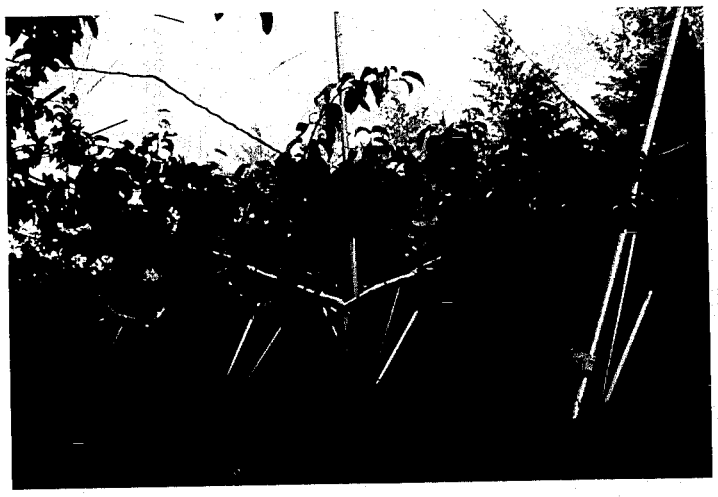
FIG. 2 is a photograph of a shape of the new variety of Japanese pear tree.
Figure 3:
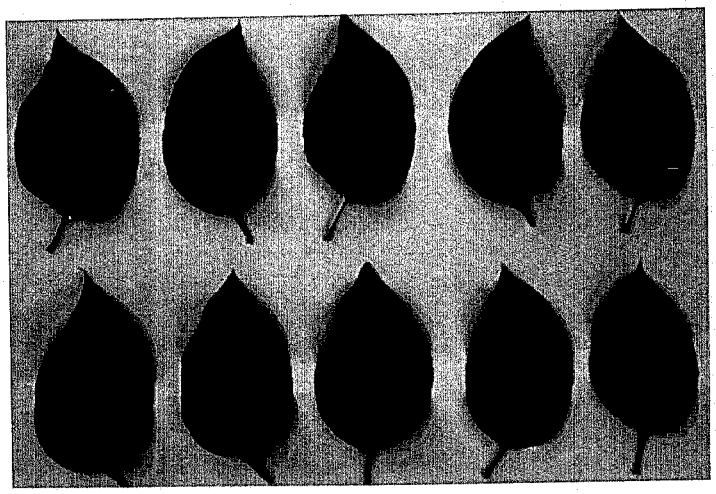
FIG. 3 is a photograph of adult leaves, the upper row being adaxial and the lower one being abaxial, of the new variety of Japanese pear tree.
Figure 4:
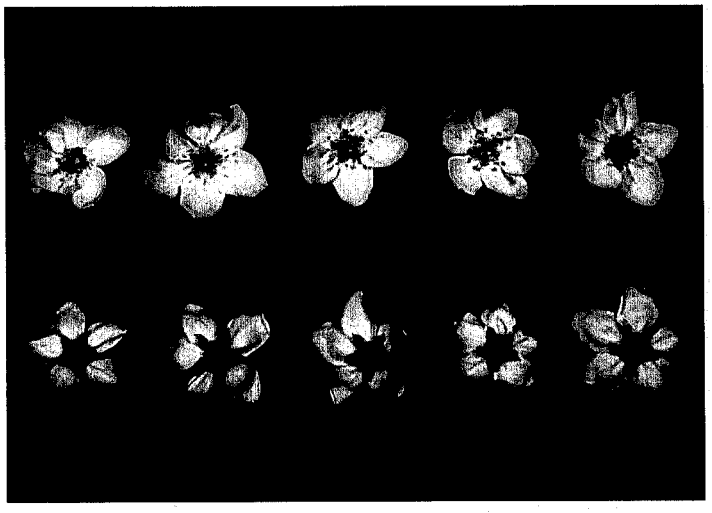
FIG. 4 is a photograph of the flower of the new variety of Japanese pear tree.
Figure 5:
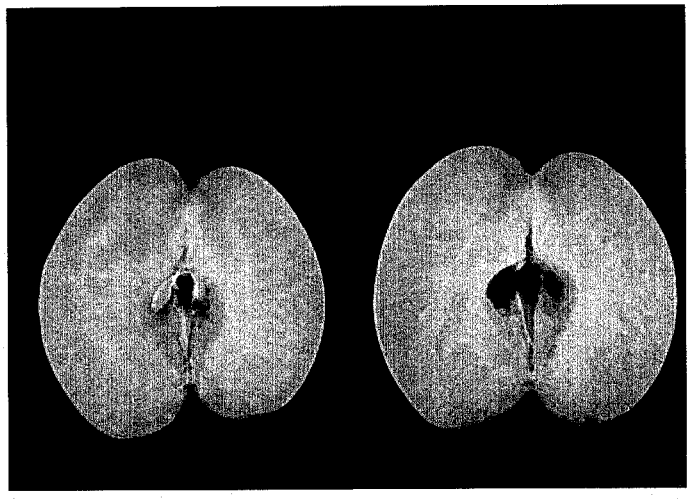
FIG. 5 is a photograph of longitudinal-sectional views of fruit of the new variety of Japanese pear tree.
Figure 6:
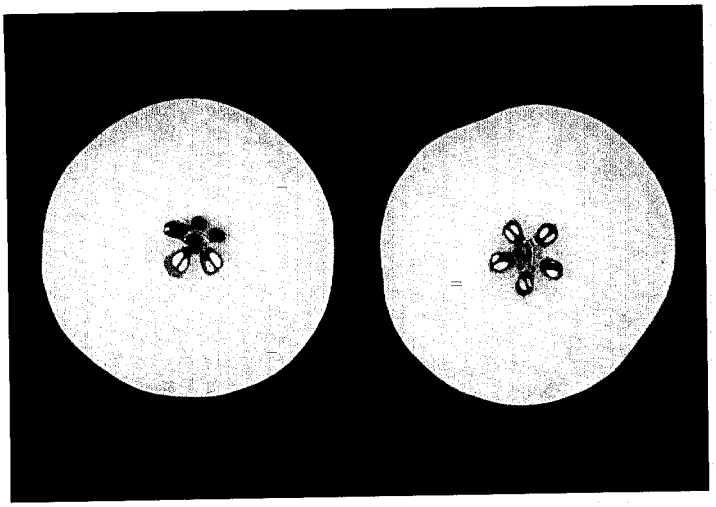
FIG. 6 is a photograph of cross-sectional views of fruit of the new variety of Japanese pear tree.
Figure 7:
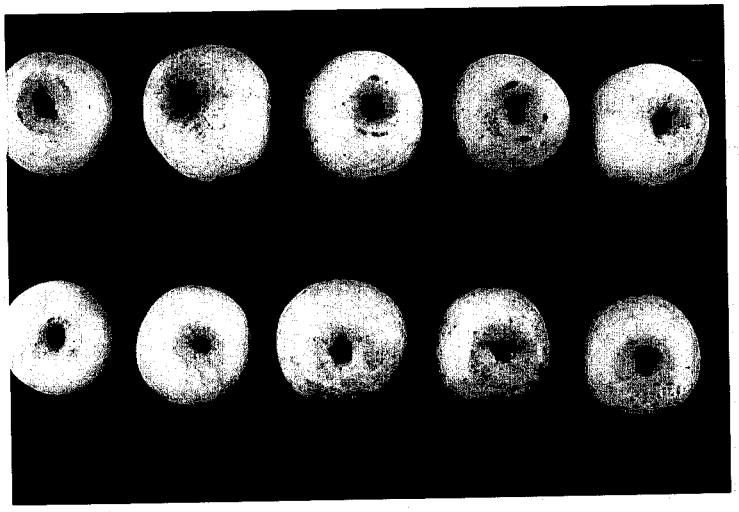
FIG. 7 is a photograph of views at the blossom end of fruit of the new variety of Japanese pear tree.
Figure 8:
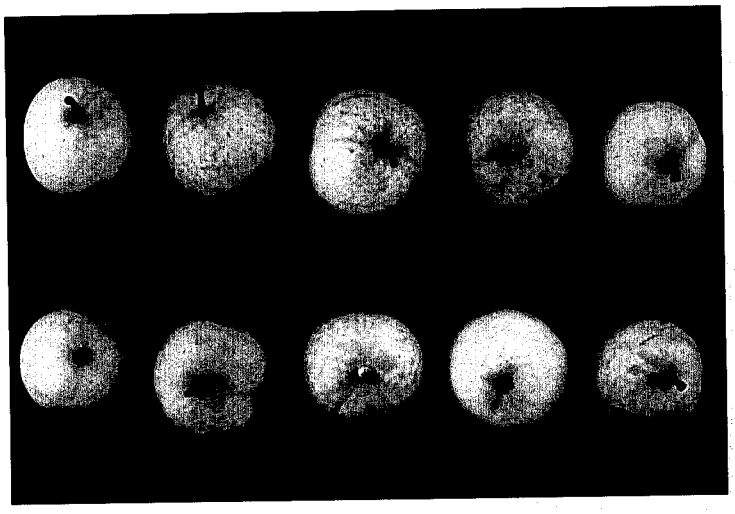
FIG. 8 is a photograph of views at the stem end of fruit of the new variety of Japanese pear tree.

The characteristics of the new and distinct variety of Japanese pear tree 'Yasato' are as follows (herein, "J.H.S.C." is an abbreviation of "Japan Horticulture Standard Color Chart."):

Tree:

*Vigor.*—Strong; stronger than 'Chikusui' and 'Shuugyoku'. The unpruned tree may have a height of about 7 m and a width of about 4 m when 15 years old. When the was grafted on a root stock, which is a seedling stock of Japanese pear, and cultivated for ten years, a vegetative shoot of the tree extended to 70–80 cm per year.

*Spur.*—Easy to maintain. The number of spurs is 12 per meter of branch.

*Predominance of axillary flower bud.*—Slight increment beyond medium.

*Time of bud break.*—Slightly late; same as 'Kōsui' and 'Chikusui'.

*Production.*—High productivity; greater than that of 'Yakumo' and 'Shinseiki'. The tree is year-round bearing.

*Cross-compatibility.*—Cross-compatible with, e.g., 'Kōsui', 'Shinsui' and 'Nijisseiki'. The tree is self-incompatible and is manually pollinated. The fruit set percentage is 10% or less, if self-pollinization occurs in the tree.

*Bark.*—The bark texture of new and old wood is the same hardness as 'Nijisseiki' and 'Kōsui'; the bark of the about ten year old tree may be cracked. The lenticels of new and old wood are slightly smaller than those of 'Kōsui', and their density is slightly higher than that of 'Chikusui'.

Branches:

*Thickness.*—Stout.

*Length of internode.*—Long; 6.1 cm.

*Lenticel.*—Medium; fewer than 'Chikusui'.

*Color.*—Dark reddish brown (J.H.S.C. 1009; ISCC-NBS, dark reddish brown).

*Density of pubescence.*—Low; same as 'Chikusui' and 'Shuugyoku'.

Leaves:

*Shape.*—Oval.

*Size.*—Medium (121 mm×74 mm); smaller than 'Shuugyokui'.

*Color.*—Dark bluish green (J.H.S.C. 4907; ISCC-NBS, dark green).

*Petiole.*—Short (27 mm).

*Young leaves.*—Reddish brown (J.H.S.C. 0710; ISCC-NBS, dark reddish brown) and having low pubescence density.

Flowers:

*Flower number in a flower cluster.*—Medium; from 6–8 per cluster.

*Size.*—Medium (about 3.4 cm on average); smaller than 'Chikusui' and 'Shuugyoku'.

*Color.*—White; purplish pink (J.H.S.C. 9703; ISCC-NBS, light purplish pink) calyx coloration at blooming. Fades to pure white with flower opening.

*Shape of petals.*—Oval and medium.

*Notch of margin of petals.*—Medium.

*Number of petals.*—Medium (5.1 pieces on average); same as 'Chikusui'.

*Color of anther.*—Strong pink (J.H.S.C. 0105; ISCC-NBS, deep pink).

*Number of pollen.*—Medium.

*Flowering time.*—Late in the season; about 2 days later than 'Chikusui'.

*Flowering date and full bloom stage. April* 17 and 19 (an average from 1988 to 1990) at Tukuba-shi in Japan.

Fruit:

*Size.*—About 270 g; smaller than 'Shuugyoku' and slightly larger than 'Chikusui'.

*Shape.*—Circular-ellipse-shape with a shallow depth and narrow breadth basin cavity, and a shallow depth stalk cavity.

*Color of skin (unbagged fruit).*—Light greenish yellow (J.H.S.C. 2703; ISCC-NBS, light greenish yellow).

*Calyx perpetual fruit.*—Absent.

*Size of dot.*—small; smaller than 'Chikusui'.

*Density of dot.*—Medium.

*Color of flesh.*—Yellowish white (J.H.S.C. 2701; ISCC-NBS, yellowish white).

*Flesh.*—Soft, crisp and juicy. The flesh is as juicy as those of 'Chikusui' and 'Shuugyoku'. The firmness is about 4.9 lbs. according to Magnessteller's hardness meter index; almost the same level as 'Chikusui'. When the fruit is stored at 25° C. for seven days immediately after picking, there is no mealiness in the core of the flesh.

*Color of peduncle.*—Dull gray (J.H.S.C. 4010; ISCC-NBS, moderate yellowish green).

*Color of dot.*—Yellowish gray (J.H.S.C. 2914; ISCC-NBS, yellowish gray)

Color of core.—Yellowish white (J.H.S.C. 3301;ISCC-NBS, yellowish white).

*Seed cells.*—Five celts per fruit; up to two seeds per cell with complete pollination; average about 6 developed seeds per well shaped fruit.

*Taste.*—Having a high sweetness that is almost the same level as 'Shuugyoku', the sugar content of the fruit juice is about 12%, a medium acidity that is substantially the same level as 'Nijisseiki', the pH of the fruit juice is more than 4.7, no astringency, and no aromatic flavor, which gives an excellent dessert quality. Although the taste of the fruit at the skin/flesh interface cannot be distinguished, the taste of the core flesh tissues surrounding the seed cells has slightly higher acidity than other parts.

*Bagged.*—The bagged fruit has a slightly fine appearance compared to fruit which has not been bagged, but the former has a lower sweetness than the latter. The coloration and russetting of both fruits are not distinguishable from each other, but in the unbagged fruit cork spots are slightly apparent than in the bagged fruit. The fruit is of typical juice content and characteristic flavor for an oriental pear per se, but which is accentuated by normal to superior sweetness while being of less than normal acidity; these combined attributes taken with the delicate, crisp flesh texture, and substantial absence of astringency and surface blemishes, result in the fruit of 'Yasato' being an important introduction to the presently available list of desert pear varieties available to the grower.

*Maturity.*—Ripening early in the season; slightly earlier than 'Yakumo' and about 10 days earlier than 'Shuugyoku', e.g., from the middle to the end of August, in the central Kantō district, Japan.

*Use.*—Suitable for dessert.

*Keeping quality.*—Can be kept for about 7 days at 25° C., which is slightly higher than those of 'Chikusui' and 'Shinsui'.

Resistance to diseases: Has a strong resistance to black spot disease and is not sensitive to pear necrotic spot. Pear scab and the like can be treated by usual control measures for pear disease.

Cold resistant: Has almost the same as that of the other Japanese pears.

Core breakdown: Although slight core breakdown may be observed immediately before picking stage, there are no problems in practical use.

Watercore: Watercore may be slightly observed immediately before picking stage.

Fruit cracking: None.

Culture: The shape and uniformity of the fruit shows a tendency to disperse, but these problems can be solved by usual fruit thinning methods.

The new variety of Japanese pear tree is cultivated and kept at our farm located at 2-1, Fujimoto, Tsukuba, 3-5 Japan.

Since the new variety, 'Yasato', has a strong resistance to disease which generally attack pear trees, an excellent dessert quality, and the harvesting stage of the fruit is early in the season, the trees of this variety can be conveniently planted in place of the Japanese pear tree 'Yakumo', which bears a fruit with a yellowish-green skin, in an orchard:

We claim:

1. A new and distinct variety of Japanese pear tree, substantially as illustrated and described herein, characterized over the known Japanese pear trees by having a strong vigor, a good maintained spur, a strong resistance to scab; having dark bluish green leaves and white flowers; a large amount of fruit which has a light green yellow skin and a circular-ellipse-shape; and a flesh which is yellowish white in color, soft, crisp and very juicy, with a high sweetness, a medium acidity, no astringency, and a harvesting stage of the fruit early in the season.

* * * * *

Fig.1. Pedigree of 'Yasato'.